United States Patent
Schrattenecker et al.

(10) Patent No.: US 11,660,014 B2
(45) Date of Patent: May 30, 2023

(54) TOMOGRAPHY APPARATUS AND TOMOGRAPHY METHOD

(71) Applicant: Infineon Technologies AG, Neubiberg (DE)

(72) Inventors: Jochen O. Schrattenecker, Reichenthal (AT); Andreas Och, Linz (AT); Stefan Schuster, Enns (AT)

(73) Assignee: Infineon Technologies AG, Neubiberg (DE)

( * ) Notice: Subject to any disclaimer, the term of this patent is extended or adjusted under 35 U.S.C. 154(b) by 466 days.

(21) Appl. No.: 16/849,473

(22) Filed: Apr. 15, 2020

(65) Prior Publication Data
US 2020/0337589 A1 Oct. 29, 2020

(30) Foreign Application Priority Data
Apr. 24, 2019 (DE) .......................... 102019110621.4

(51) Int. Cl.
| | | |
|---|---|---|
| *A61B 5/0536* | (2021.01) | |
| *A61B 5/0507* | (2021.01) | |
| *G01N 22/00* | (2006.01) | |
| *G01S 13/89* | (2006.01) | |

(52) U.S. Cl.
CPC .......... *A61B 5/0536* (2013.01); *A61B 5/0507* (2013.01); *G01N 22/00* (2013.01); *G01S 13/89* (2013.01)

(58) Field of Classification Search
None
See application file for complete search history.

(56) References Cited

U.S. PATENT DOCUMENTS

| | | | |
|---|---|---|---|
| 7,671,784 B2 | 3/2010 | Steinway et al. | |
| 2010/0303321 A1* | 12/2010 | McEwan | A61B 5/0536 382/131 |
| 2011/0227586 A1 | 9/2011 | Lovetri et al. | |
| 2012/0194823 A1* | 8/2012 | Moore | G01B 9/02091 356/450 |

FOREIGN PATENT DOCUMENTS

| | | |
|---|---|---|
| WO | 2013005134 A2 | 1/2013 |
| WO | 2016005909 A1 | 1/2016 |

* cited by examiner

*Primary Examiner* — Whitney Moore
(74) *Attorney, Agent, or Firm* — Harrity & Harrity, LLP (57) ABSTRACT

The present disclosure relates to a computed tomography apparatus, comprising: a first semiconductor device with a first radar transceiver IC, a second semiconductor device with a second radar transceiver IC, and at least one third semiconductor device with a third radar transceiver IC, which are arranged at different positions around a tomographical measurement region; a synchronization circuit, which is designed to provide a synchronization signal in order to operate the first, second and third radar transceiver IC as synchronized transmitters and receivers using the synchronization signal; and an evaluation circuit, which is designed to ascertain at least one characteristic of a medium located in the measurement region based on time-of-flight measurements of radar signals received from at least two receivers.

20 Claims, 6 Drawing Sheets

TOMOGRAPHY APPARATUS AND TOMOGRAPHY METHOD

CROSS REFERENCE TO RELATED APPLICATION

This application claims priority to German Patent Application No. 102019110621.4 filed on Apr. 24, 2019, the content of which is incorporated by reference herein in its entirety.

TECHNICAL FIELD

The present disclosure relates in general to tomographic systems and, for example, to tomographic systems based on microwaves.

BACKGROUND

For many applications, non-invasive sensor systems for process monitoring and control are used. Computed tomography systems can image, for example, a spatial distribution of material within a certain measurement region, for example a process pipe, and can provide information about process parameters. For example, industrial and automotive applications use observation of reagents and products of chemical processes in order to optimize process efficiency and control. Materials are often transported or mixed within pipes. It is time-consuming to take samples to a laboratory, which means that in-situ measurement systems may be preferred. In the past few decades various imaging systems have been developed, including electrical impedance, ultrasonic, optical, magnetic resonance and X-radiation, gamma radiation or microwave tomography systems.

Tomographic systems which are based on technologies such as capacitive impedance measurements have been available for many years, but due to accuracy limitations they can only be used for a limited number of applications. In many processes, sensors are placed at a small number of positions and data are extrapolated using previous experience and laboratory experiments. While this is sufficient for a basic process control, it does not allow the maximum optimization of the process, however.

In addition, many known tomographic systems are complex in design and expensive.

BRIEF SUMMARY

According to a first aspect, a tomography apparatus is proposed. The tomography apparatus comprises a first semiconductor device with a first radar transceiver integrated circuit (IC), a second semiconductor device with a second radar transceiver IC, and at least one third semiconductor device with a third radar transceiver IC, which are arranged at different positions around a tomographical measurement region. Further semiconductor devices with radar transceiver ICs are possible and advantageous in appropriate cases. The tomography apparatus comprises a synchronization circuit which is designed to provide a synchronization signal in order to operate the first, second and third radar transceiver IC as synchronized transmitters and receivers for radar signals through the measurement region using the synchronization signal. The tomography device also comprises an evaluation circuit which is designed to ascertain at least one characteristic of a medium located in the measuring range based on time-of-flight measurements of radar signals received from at least two receivers.

A tomographical system is therefore proposed, which is based on radar MMICs (monolithic microwave integrated circuits), in order to characterize material in the measurement region (for example, a pipe) non-invasively. There are many potential applications in the automotive and industrial sectors, such as a flow-rate measurement of substances in powder form, a temperature distribution of gases or the analysis of material compounds. In comparison to conventional sensors, the proposed tomographic system can not only characterize material at a sensor position, but, for example, reconstruct a 2D image of material properties along a cross-section of the measurement region. Multiple systems can be combined to enable 3D measurements.

The proposed tomography apparatus uses a plurality of radar sensors, which each comprise one or more fully-integrated radar transceivers. These radar transceivers are located in the vicinity of the measurement region, in which one or more different types of media are present. Different media show different electromagnetic behaviors depending on the nature of the medium, its temperature, humidity, pressure, etc. By using time-of-flight measurements of radar signals through the measurement region, at least one characteristic of the medium present in the measurement region can be ascertained.

In accordance with some example implementations the first radar transceiver IC is designed to generate a local oscillator signal in the microwave range. The synchronization signal is based on the local oscillator signal of the first radar transceiver IC or is derived from this. Therefore, the first radar transceiver IC can function as a synchronization master and a highly accurate (phase-locked) synchronization of the radar transceiver ICs can be achieved.

According to some example implementations, the first radar transceiver IC is designed as a master-IC in order to generate the local oscillator signal and distribute the signal or a signal derived from it using the synchronization circuit as a synchronization signal to the second and third radar transceiver ICs, which are each designed as a slave. The local oscillator signal itself of the first radar transceiver IC can thus be distributed directly to the other radar transceiver ICs, so that they all use the same local oscillator signal. In this case, the local oscillator signal can correspond, for example, to a CW (Continuous Wave) or FMCW (Frequency Modulated Continuous Wave) radar signal. If all radar transceiver ICs use the same local oscillator signal for transmission and/or reception, a highly accurate, phase-locked synchronization of the radar transceiver ICs is possible.

According to some example implementations, the synchronization circuit is designed to divide down a frequency of the local oscillator signal, in order to obtain a divided-down local oscillator signal and distribute it as a synchronization signal to the second and third radar transceiver ICs. A divided-down signal frequency of the local oscillator can then be transformed up again in the slaves. The divided-down frequency can then be used to simplify a distribution of the synchronization signal. For example, simpler signal cables can be used.

According to some example implementations the synchronization signal is based on a clock signal of the first radar transceiver IC and the synchronization circuit is designed to generate respective local oscillator signals in the first and second and third radar transceiver IC based on the clock signal. Here the synchronization signal corresponds to a common clock signal, on the basis of which each of the radar transceiver ICs can generate its own high-frequency local oscillator signal. The distribution of the clock signal, which has a comparatively low frequency, can then be less complicated than the distribution of the higher-frequency local oscillator signal.

According to some example implementations the evaluation circuit is designed to ascertain the at least one characteristic of the medium based on a difference between a time-of-flight measurement and a calibration time-of-flight measurement. A calibration can thus be carried out prior to the initial operation of the tomography device, in which the behavior of the radar signals with regard to propagation time and, if appropriate, attenuation in different known media, can be recorded or stored. These results can then be compared with current time-of-flight measurements during operation.

According to some example implementations the evaluation circuit is designed to ascertain the at least one characteristic of the medium, based on a phase difference and/or a power difference between a transmission signal of the first radar transceiver IC and a received signal of the second and/or third radar transceiver IC. The time-of-flight measurements can thus be carried out by determining phase differences between transmitted and received signals (for example, in the case of CW radar signals). In addition, power differences can be monitored, in order to draw conclusions about an attenuation characteristic of the medium.

According to some example implementations the evaluation circuit is designed to ascertain the at least one characteristic of the medium, based on a frequency difference and/or a power difference between a transmission signal of the first radar transceiver IC and a received signal of the second and/or third radar transceiver IC. The time-of-flight measurements can thus be carried out by determining frequency differences between transmitted and received signals (for example, in the case of FMCW radar signals). In addition, differences in power can be monitored in order to draw conclusions about an attenuation characteristic of the medium.

In the case of FMCW radar transceiver ICs, each of the radar transceiver ICs can have a built-in FFT (Fast Fourier Transform) circuit, which is designed to subject a respective baseband received signal to an FFT to obtain an FFT signal. This FFT signal (spectrum) can then provide information about the medium. Each of the radar transceiver ICs can be designed to forward its FFT signal to the evaluation circuit. The evaluation circuit is designed to ascertain the medium from a combination of the FFT signals. In accordance with other implementations however, the baseband signals of the individual radar transceiver ICs can also be transferred to a central FFT circuit in order to perform the FFTs of the baseband signals and then the combination of the FFT signals. This can reduce the complexity of the radar transceiver ICs.

In accordance with some example implementations, the tomography apparatus further comprises a control circuit, which is designed to operate the first, second and third radar transceiver IC as a transmitter and receiver according to a multiplexing method. The multiplexing method can comprise a frequency-division multiplexing (FDMA), time-division multiplexing (TDMA), or code-multiplexing method (CDMA), or a combination of these. In FDMA different radar transceiver ICs can transmit at the same time, but with different frequencies or frequency ramps. In TDMA different radar transceiver ICs can transmit in different time slots. In CDMA different codes can be modulated onto radar signals of different transmitters, in order to make them distinguishable.

In accordance with some example implementations the medium is located in a container, which is non-transparent to the radar signals and has transmission regions for the radar signals at the different positions of the radar transceiver ICs. The transmission regions can be formed by openings, by Plexiglas or other transparent materials.

According to some example implementations the radar transceiver ICs are each coupled to antennas, which each have a directional characteristic that is matched to a distribution of the radar transceiver ICs around the medium. The directional characteristic is intended to ensure that as many radar signals emitted by a radar transceiver IC into the measurement region are received by other radar transceiver ICs. This enables the accuracy of the microwave tomography to be increased.

According to a further aspect, a tomography method is proposed. The method comprises the arrangement of a first semiconductor device with a first radar transceiver IC, of a second semiconductor device with a second radar transceiver IC, and of at least one third semiconductor device with a third radar transceiver IC at different positions around a tomographical measurement region. A synchronization signal is distributed to the first, second and third radar transceiver IC in order to operate the first, second and third radar transceiver IC as synchronized transmitters and receivers for radar signals through the measurement region using the synchronization signal. Time-of-flight measurements of radar signals received from at least of two receivers are carried out and evaluated in order to ascertain a characteristic of a medium located in the measuring region.

According to some example implementations, a local oscillator signal is generated in the first radar transceiver IC, on which the synchronization signal is based. In this case, the local oscillator signal can be generated as an FMCW radar signal.

According to some example implementations to perform a tomography of the medium the radar transceiver ICs are operated as a transmitter and receiver according to a multiplexing method.

According to some example implementations the at least one characteristic of the medium can be ascertained, based on a phase difference and/or a power difference between a transmission signal of the first radar transceiver IC and a received signal of at least the second and/or third radar transceiver IC.

In accordance with example implementations therefore, fully integrated RF hardware is used and system costs, size and complexity are thus reduced. The proposed radar MMICS may operate, for example, with frequencies in the range of 76-80 GHz, which allows high tomographic resolutions to be achieved. The increased resolutions allow them to be used for additional demanding industrial applications, such as measurements of the temperature distribution of a gas stream or gas concentrations in gas mixtures.

BRIEF DESCRIPTION OF THE DRAWINGS

Some examples of apparatuses and/or methods are described in more detail in the following with reference to the accompanying figures, purely as examples. In the drawings.

DETAILED DESCRIPTION

Various example implementations will now be described in more detail with reference to the accompanying drawings, in which several examples are shown. In the figures, the thickness dimensions of lines, layers and/or regions may be shown exaggerated for the sake of clarity.

While other examples are suitable for various modifications and alternative forms, several specific examples of the same are therefore shown in the figures and are described in detail in the following. However, this detailed description does not limit further examples to the specific described forms. Further examples can cover all modifications, equivalents and alternatives which are included in the scope of the disclosure. Identical or similar reference signs refer throughout the description of the figures to the same or similar elements which, when compared to each other may be implemented identically or in modified form although they provide the same or a similar function.

It is self-explanatory that when an element is designated as being "connected" or "coupled" to another element, the elements can be connected or coupled directly, or via one or more intermediate elements. If two elements A and B are combined using an "or", this should be understood to mean that all possible combinations are disclosed, e.g. only A, only B, as well as A and B, unless otherwise explicitly or implicitly defined. An alternative formulation for the same combinations is "at least one of A and B" or "A and/or B". The same applies, mutatis mutandis, to combinations of more than two elements.

The terminology that is used here to describe specific examples, is not intended to be limiting for other examples. If a singular form, e.g. "a, an" and "the" is used and the use of only a single element is neither explicitly nor implicitly defined as mandatory, then other examples may also use plural elements to implement the same function. If a function is described below as being implemented using a plurality of elements, further examples may implement the same function by using a single element or a single processing entity. It also goes without saying that the use of the terms "comprises", "comprising", "has" and/or "having" precisely defines the presence of the specified features, integers, steps, operations, processes, elements, components and/or a group of the same, but not the presence or the addition of one or more other features, integers, steps, operations, processes, elements, components and/or a group of the same.

Unless otherwise defined, all terms (including technical and scientific terms) are used here in their usual meaning in the field to which the examples belong.

Figure 1:
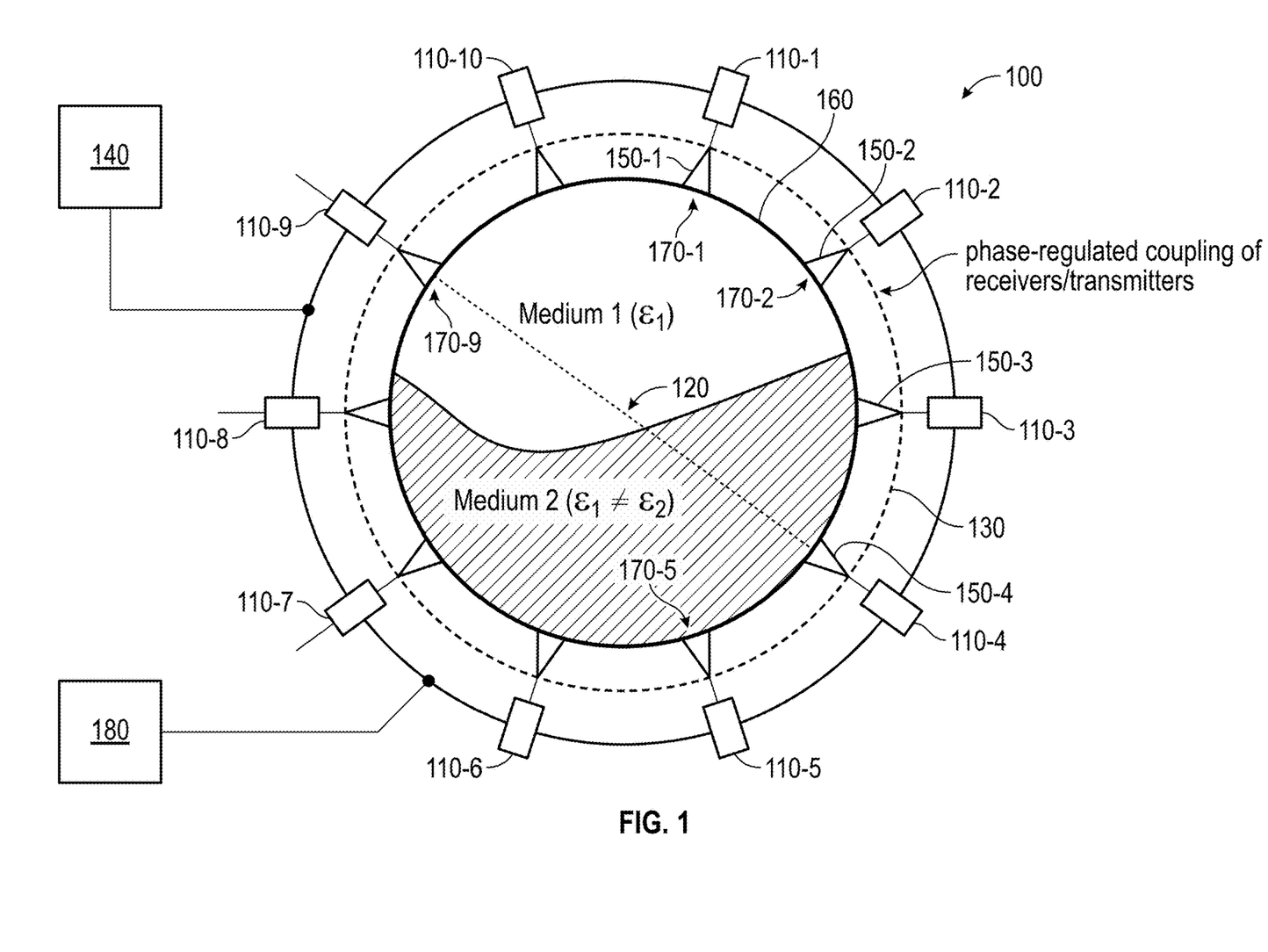
FIG. 1 shows a schematic drawing of a tomography apparatus according to example implementations.

FIG. 1 illustrates schematically a computed tomography apparatus 100 in accordance with example implementations of the present disclosure.

The proposed tomography device 100 comprises a plurality of semiconductor devices with integrated radar transceiver circuits (radar transceiver ICs) 110. The radar transceiver ICs 110 each integrate transmitters, receivers, amplifiers, analog-to-digital converters/digital-to-analog converters, microprocessors and, where appropriate, antenna(s) in a semiconductor chip. FIG. 1 shows an example apparatus with ten radar transceiver ICs 110-1-110-10. The radar transceiver ICs 110 are arranged at different known locations around a tomographical measurement region 120. In the implementation shown the measurement region 120 is a pipe. It is self-explanatory, however, that any other measurement regions or measurement objects are possible. The tomography apparatus 100 comprises a synchronization circuit 130 which is designed to provide a synchronization signal in order to operate the radar transceiver IC, the radar transceiver ICs 110-1-110-10 as synchronized transmitters and receivers for radar signals through the measurement region 120 using the synchronization signal. The tomography apparatus 100 also comprises an evaluation circuit 140, which is designed to ascertain at least one characteristic of a medium located in the measuring region 120 based on time-of-flight measurements of radar signals received from different receivers.

To send and receive the radar signals into and out of the measurement region 120 the radar transceiver ICs 110 are each coupled to one or more integrated or discrete antennas 150, each of which has a directional characteristic which is matched to a geometrical arrangement of the radar transceiver ICs 110 around the measurement region 120. In the example implementation shown here, the antennas 150 can each have a wide-angled antenna characteristic directed forwards as far as possible, in order to radiate as much power as possible into the measurement region 120 and to the respective adjacent antennas.

The medium or media is/are located in a measurement object or container 160 which is non-transparent to the radar signals and in the example here is shown as a pipe. The pipe 160 has transparent transmission regions 170 for the radar signals at the different positions of the radar transceiver ICs 110 or the antennas. For example, this could be individual quartz or Plexiglas windows arranged in the pipe cladding, or a glass ring. Other implementations of the transmission regions 170 are also possible.

A control circuit 180 can be provided to operate the radar transceiver ICs 110 as a transmitter and receiver in accordance with at least one multiplexing method. Different multiplexing methods can be used for this purpose. According to a first example implementation, the radar transceiver ICs 110 could be operated as transmitters sequentially or in accordance with any other time-division multiplexing switching pattern. The remaining non-transmitting radar transceiver ICs work as receivers. Thus, for example, in a first time interval the radar transceiver IC 110-1 could function as a transmitter, while the remaining radar transceiver ICs work as receivers. In a subsequent, second time interval the second radar transceiver IC 110-2 could function as a transmitter, while the remaining radar transceiver ICs work as receivers. In a subsequent, third time interval the third radar transceiver IC 110-3 could function as a transmitter etc., until all radar transceiver ICs have been receivers in turn. Other time-division multiplex switching patterns of the radar transceiver ICs 110 are of course also possible.

Figure 2:
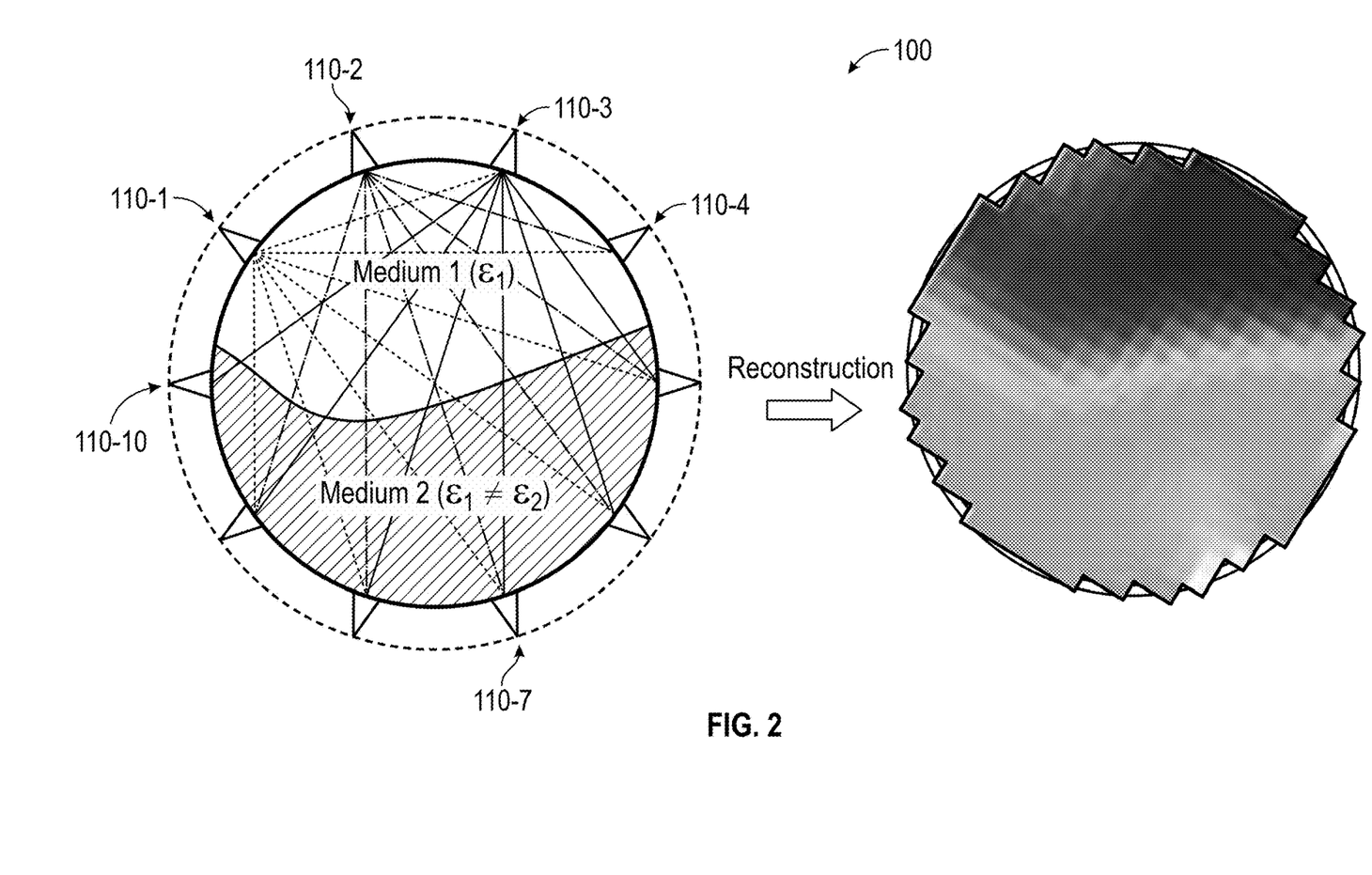
FIG. 2 shows radar transceiver ICs of the tomography apparatus operated according to a multiplexing method.

In addition or alternatively, subsets of the radar transceiver ICs 110 can be operated as transmitters at the same time. This is indicated in FIG. 2, where the radar transceiver ICs 110-1 to 110-3 are simultaneously operated as transmitters within a time interval, while the rest of the radar transceiver ICs 110-4 to 110-10 are operated as receivers. This is possible, for example, using frequency-division multiplexing (FDMA) methods and/or code-division multiplexing methods (CDMA). In FDMA, the radar transceiver ICs 110-1 to 110-3 can use different transmission frequencies or different transmission frequency ramps. In CDMA the transmission signals of the radar transceiver ICs 110-1 to 110-3 can be made distinguishable by having different (for example, orthogonal) modulated code sequences for the first radar transceiver ICs 110-4 to 110-10. In a subsequent time interval the radar transceiver ICs 110-4 to 110-6 can then function simultaneously as transmitters etc., until all radar transceiver ICs have been radar transceiver ICs in turn.

Some example implementations involve microwave or radar tomography using transmission measurements, wherein ratios of the different radar signals before and after interaction with the medium or the media are measured in the measurement region 120. This interaction is characteristic of each medium or of the dielectric conductivity or permittivity of each medium. This is briefly explained on the basis of FIG. 3.

Figure 3:
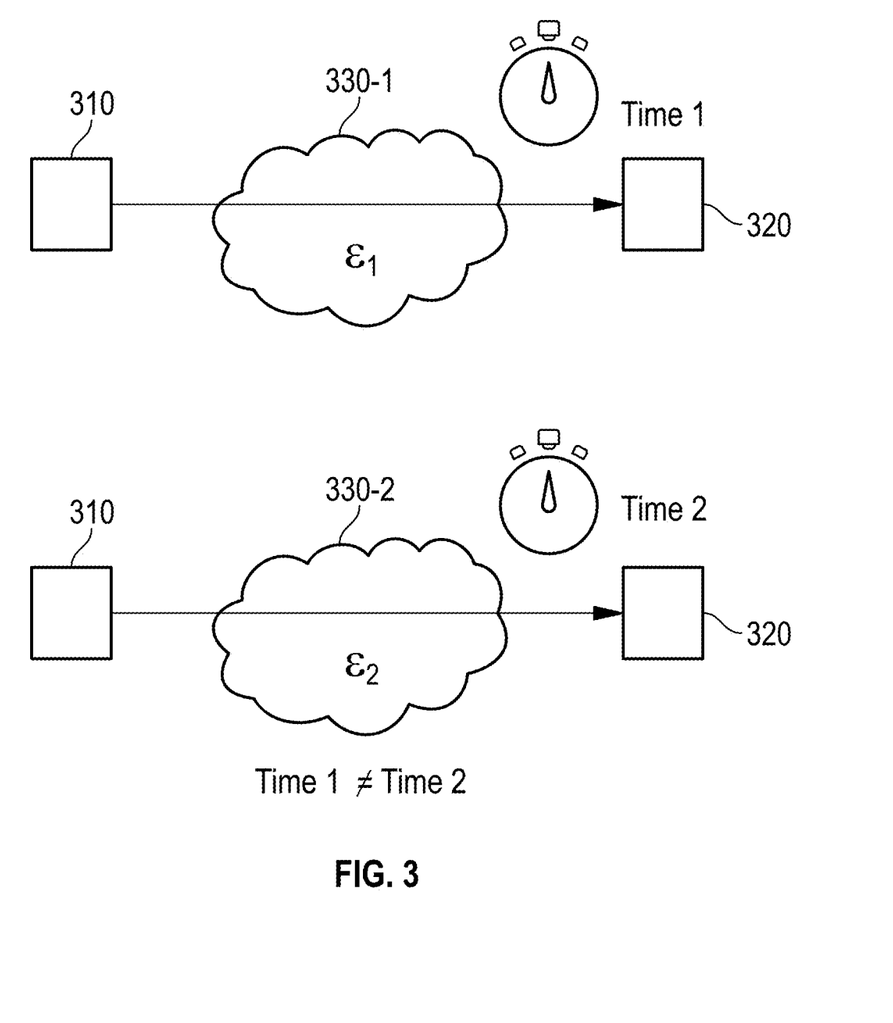
FIG. 3 shows the underlying physical concept of the disclosure of the tomography apparatus.

The propagation velocity $c_m$ of the signal in the medium depends on the dielectric permittivity $\varepsilon_m$ of the medium. The permittivity $\varepsilon_m$ changes with the medium, pressure, temperature or humidity. The propagation velocity $c_m$ depends on the medium in accordance with the well-known rule $$c_m = \frac{1}{\sqrt{\mu_m \varepsilon_m}} = \frac{c_0}{\sqrt{\mu_r \varepsilon_r}}$$

where co denotes the propagation velocity in a vacuum. Thus a radar signal from a transmitter 310 to a receiver 320 through media 330-1, 330-2 with different dielectric permittivities $\varepsilon_1$ and $\varepsilon_2$ takes a different length of time, so that based on time-of-flight measurements at least one characteristic (for example, pressure, temperature or humidity) of the media 330-1, 330-2, or the media themselves can be ascertained.

In some example implementations, it is therefore assumed that the radar transceiver ICs 110 can send and receive radio-frequency electromagnetic waves. The propagation velocity of an electromagnetic wave depends on the medium through which the wave is moving. As the distance between the radar transceiver ICs 110 is constant, a change in the time that the signal requires to travel from the transmitter to the receiver is a direct consequence of a change in the material properties of the medium along the propagation path. The combination of multiple time-of-flight measurements allows the tomographic reconstruction of a 2D distribution. For this purpose the evaluation circuit 140 can use the time-of-flight measurements of radar signals passing through the measurement region 120 to generate cross-sectional images, e.g. using computer-aided analysis. By analysis of a plurality of radar signals transmitted or received from different directions, cross-sectional images can be reconstructed. An example is illustrated in FIG. 2 (right). In the figure, two different media are shown located in the measurement region 120, a medium 1 with a first dielectric permittivity $\varepsilon_1$ and a medium 2 with a second dielectric permittivity $\varepsilon_2 \neq \varepsilon_1$. This means that the radar signals propagate differently in medium 1 than in medium 2. Conclusions about the media can be drawn, for example, from comparisons with calibration measurements. During a calibration phase time-of-flight measurements can be carried out with known media. The results can be stored and later compared with time-of-flight measurements, in order to draw conclusions about media in the measurement region 120.

The time-of-flight measurements require the (phase) synchronization of the radar transceiver ICs 110 to be as accurate as possible. For example, one of the radar transceiver ICs (for example, radar transceiver IC 110-1), can be designed to generate a local oscillator signal (LO-signal) and the synchronization circuit 130 can be designed to distribute a synchronization signal based on the LO-signal of the first radar transceiver IC 110-1 to the other radar transceiver ICs. The LO-signal can be, for example, an RF signal with a frequency greater than 10 GHz and can be used as a radar signal of the first radar transceiver IC 110-1. Depending upon the radar system used, for example an unmodulated or modulated continuous wave radar, the LO-signal can be a CW signal or an FMCW signal.

In some example implementations, the synchronization signal can be the LO-signal of the first radar transceiver IC 110-1 itself. The radar receiver IC 110-1 works, so to speak, as a synchronization master IC, the other radar transceiver ICs as slaves. In this case, a highly accurate synchronization can be achieved. All radar transceiver ICs 110 then use the same LO-signal to send and receive the radar signals. Time-of-flight measurements can thus be carried out with high accuracy based on a determination of phase differences (CW radar) or frequency differences (FMCW radar) between transmit and receive signals. In the case of FMCW radar, frequency differences and therefore time-of-flight differences can be determined, for example, using a discrete Fourier transform (e.g. FFT). For this purpose, in some example implementations each of the radar transceiver ICs 110 can have an integrated FFT circuit which is designed to subject a respective baseband reception signal to an FFT in order to obtain an FFT signal (spectrum). This FFT signal or spectrum can then provide information about the medium. Each of the radar transceiver ICs 110 can be designed to forward its FFT signal to the evaluation circuit 140 and the evaluation circuit can be designed to ascertain the medium from a combination of the FFT signals. In accordance with other implementations however, the baseband signals of the individual radar transceiver ICs can also be transferred to a central FFT circuit in the evaluation circuit 140 in order to perform the FFTs of the baseband signals and then the combination of the FFT signals. This can reduce the complexity of the individual radar transceiver ICs.

In some example implementations, a frequency of the LO-signal of the first radar transceiver IC 110-1 can be divided down for distribution as a synchronization signal to the other radar transceiver ICs, so that the frequency $f_{LO}$ of the LO-signal is a multiple of a frequency $f_{sync}$ of the synchronization signal. In the slave radar transceiver ICs the frequency $f_{sync}$ can then be transformed back up to the frequency $f_{LO}$ of the LO-signal. The distribution of the synchronization signal with the divided-down frequency may in some cases be carried out with fewer complex cables than in the case mentioned above.

In some example implementations, the synchronization signal can also be based on a clock signal of a radar transceiver IC (e.g. of the first radar transceiver IC 110-1), which is not the same as the LO-signal but has a lower frequency. The synchronization circuit 130 can then be designed to distribute this clock signal and to generate respective LO-signals in the other radar transceiver ICs based on the clock signal. The distribution of the clock signal may in some cases be carried out with even fewer complex cables than in the above cases.

Figure 4:
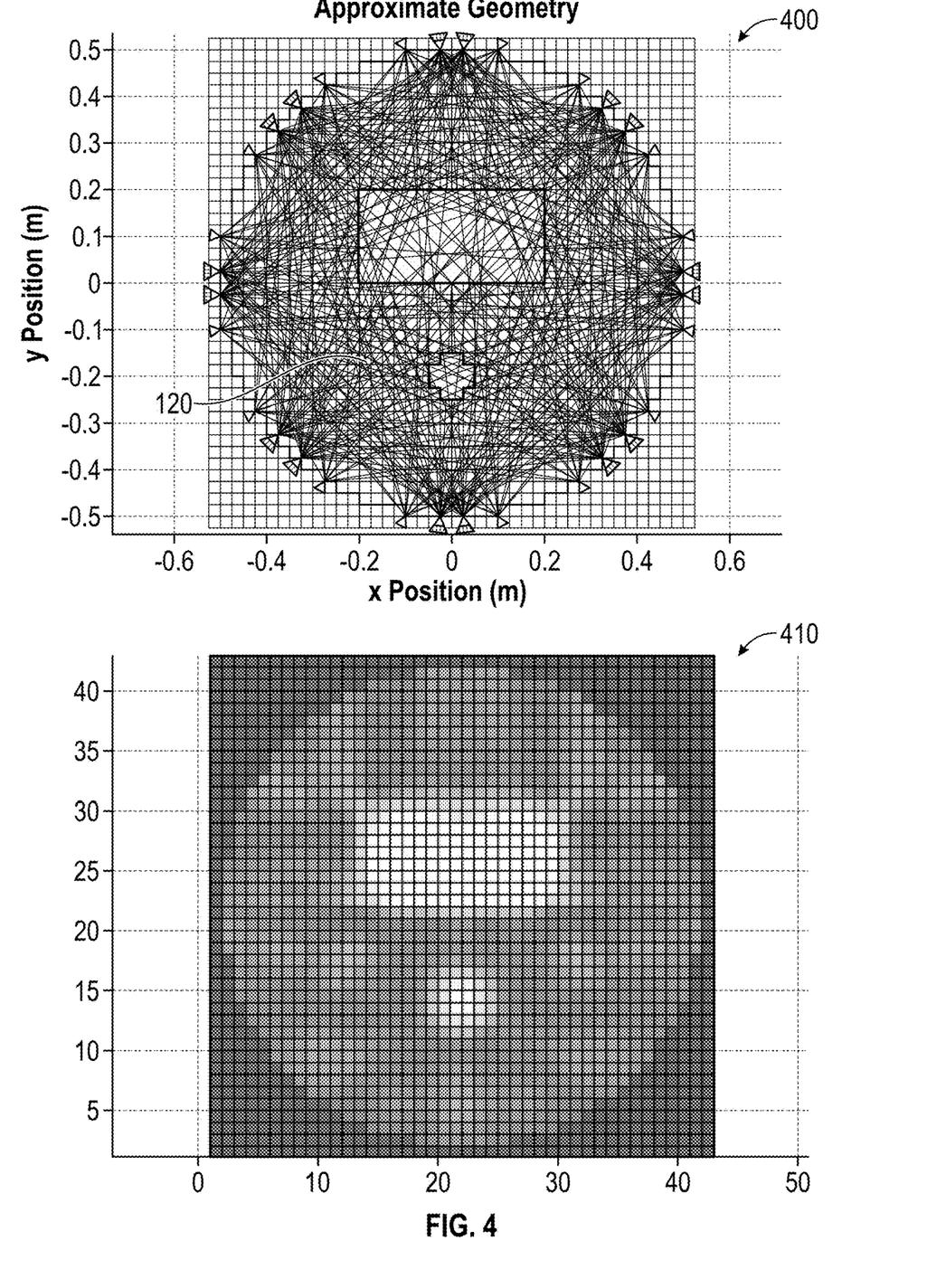
FIG. 4 shows a tomography apparatus with a large number of transceiver channels.
Figure 5:
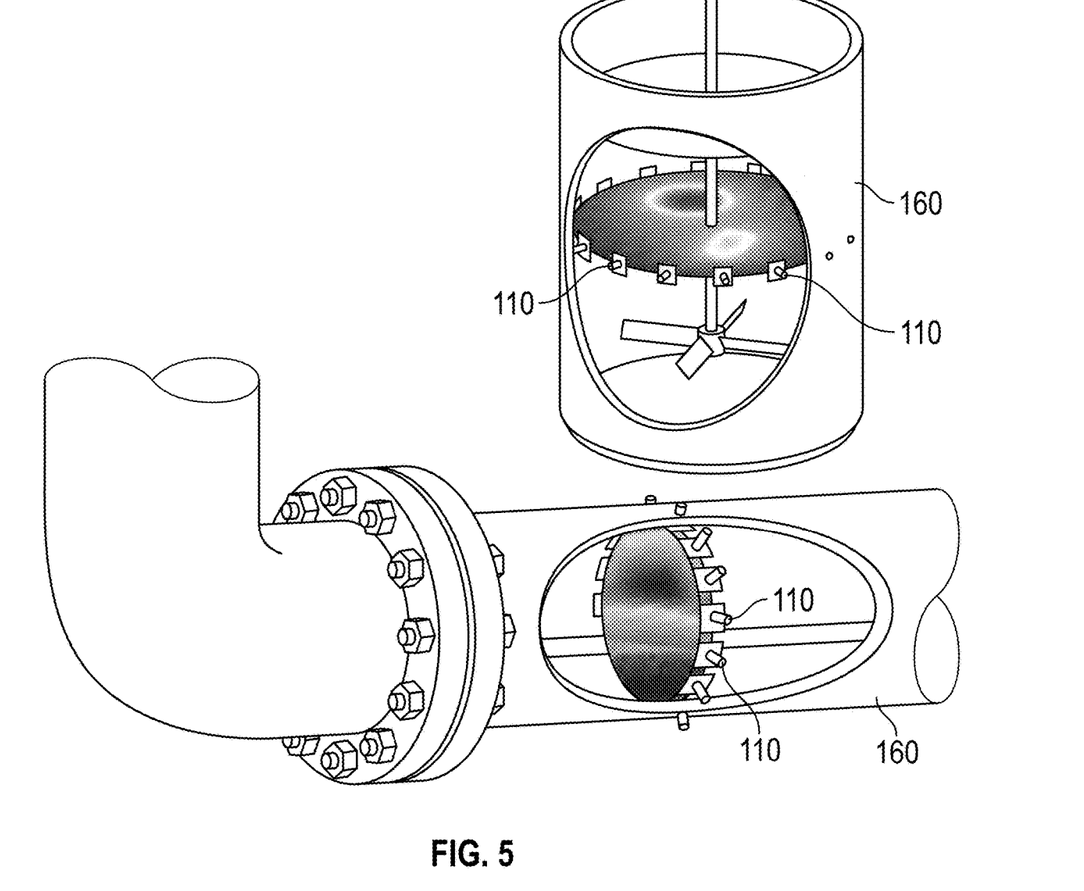
FIG. 5 shows a possible application example in the exhaust stream of an engineering production process or of a combustion process.

In accordance with some example implementations, fully integrated radar transceiver ICs for vehicles can be used to measure the signal propagation in different media. A plurality of these fully integrated radar transceiver ICs 110 are placed around a material to be tested (e.g. in a metal pipe) in order to form a microwave tomography system, so that the multidimensional distributions and parameters of the material properties can be reconstructed. The measuring system works non-invasively and is therefore ideally suited to harsh environmental conditions. Due to the high integration factor it is possible to implement a large number of antenna channels at relatively low cost. An example of a microwave tomography system 400 with many antenna channels is shown in FIG. 4. Based on the numerous radar signals, a highly accurate tomographic image 410 of the measurement region 120 can be produced (see FIG. 4, right). FIG. 5 shows a further possible application example based on the exhaust stream of an engineering production process or of a combustion process.

Figure 6:
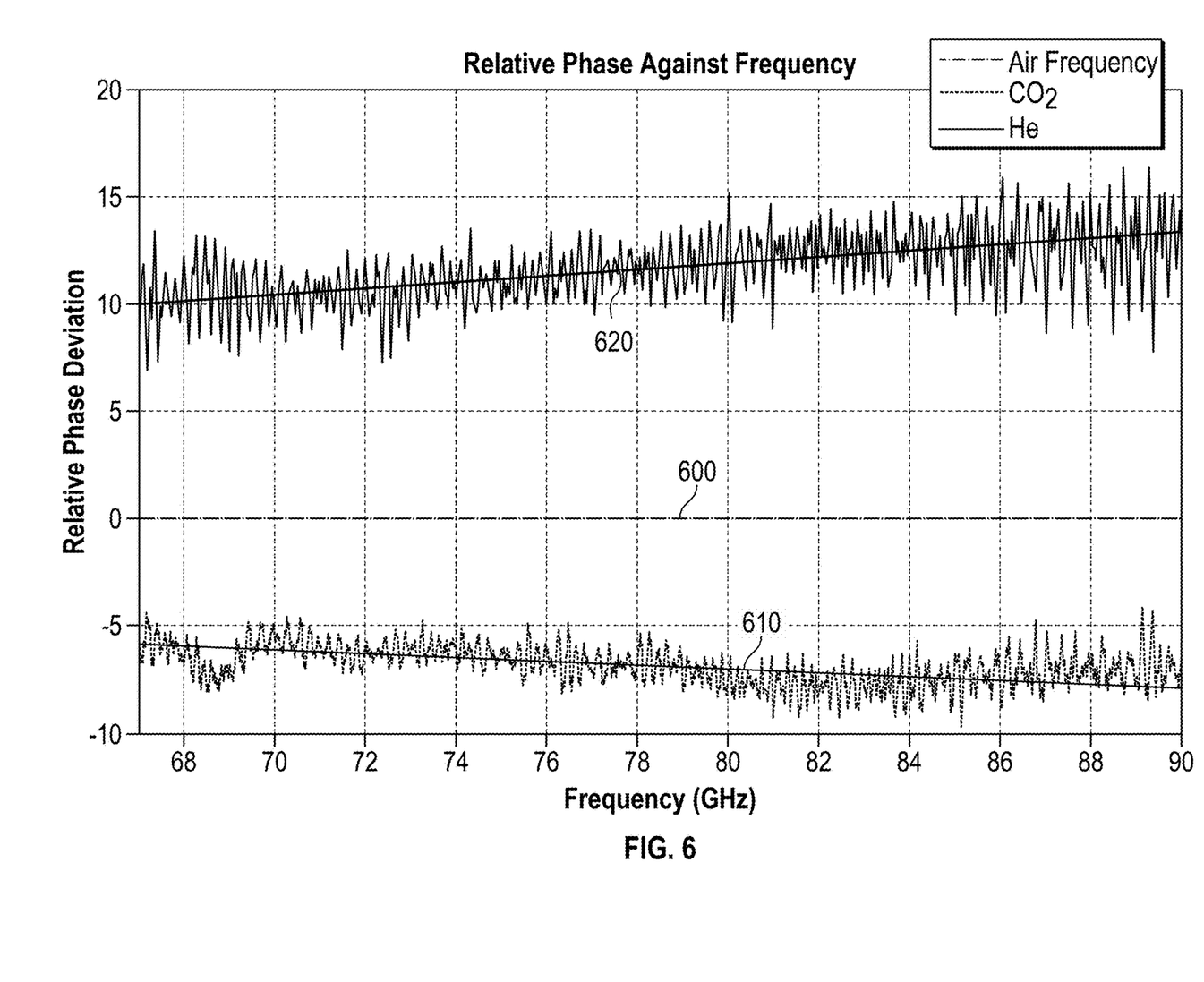
FIG. 6 shows various phase differences as a function of frequency.

The underlying principle of the tomographic reconstruction, a change in the signal propagation as a function of the permittivity of the medium, has been successfully demonstrated in a number of laboratory measurements. For this purpose, transmittance and reflectance measurements were carried out on a gas-filled Plexiglas box with different concentrations of $CO_2$ and helium. FIG. 6 shows example frequency-dependent phase deviations for $CO_2$ (curve 610) and helium (curve 620) compared to air (curve 600). The type of gas and its concentration can thereby be correctly identified using the proposed concept.

The aspects and features which are described together with one or more of the previously outlined examples and figures can also be combined with one or more of the other examples in order to replace an identical feature of the other example or to introduce the feature into the other example as an addition.

Examples can also be or relate to a computer program having a program code for executing one or more of the above methods when the computer program is executed on a computer or processor. Steps, operations or processes of various methods described above can be performed by programmed computers or processors. Examples can also include program storage devices, such as digital data storage media, which are readable by machines, processors or computers and can encode machine-executable, processor-executable or computer-executable programs of instructions. The instructions execute some or all of the steps of the above described methods or cause their execution. The program storage devices can comprise or be, for example, digital memories, magnetic storage media such as magnetic disks and magnetic tapes, hard disk drives, or optically readable digital data storage media. Other examples can also cover computers, processors or control units that are programmed to execute the steps of the methods described above, or (field-)programmable logic arrays ((F)PLAs) or (field) programmable gate arrays ((F)PGA), which are programmed to execute the steps of the methods described above.

The description and drawings illustrate only the basic principles of the disclosure. Furthermore, all the examples listed here are intended explicitly for illustrative purposes only, to assist the reader in understanding the principles of the disclosure and the concepts contributed by the inventor(s) for the further development of the technology. All statements made here concerning principles, aspects and examples of the disclosure, as well as concrete examples of the same, comprise their equivalents.

A function block designated as "means for . . . " executing a specific function can refer to a circuit that is designed to execute a specific function. Thus, a "means for something" can be implemented as a "means designed for or suitable for something", e.g. a component or a circuit designed for or suitable for the respective task.

Functions of various elements shown in the figures including all function blocks designated as "means", "means for providing a signal", "means for generating a signal", etc. can be implemented in the form of dedicated hardware, e.g. "a signal provider", "a signal processing unit", "a processor", "a controller", etc., as well as hardware capable of executing software in conjunction with the associated software. When provided by a processor the functions can be provided by a single dedicated processor, by a single jointly used processor, or by a plurality of individual processors, some of which or all of which can be used jointly. However, the term "processor" or "controller" is by no means limited exclusively to the execution of software-enabled hardware, but can comprise digital signal processor hardware (DSP hardware), network processor, application-specific integrated circuit (ASIC), field programmable logic array (FPGA=Field Programmable Gate Array), Read Only Memory (ROM) for storing software, Random Access Memory (RAM) and non-volatile memory device (storage). Other hardware, conventional and/or customized, can also be included.

A block diagram can represent, for example, a rough circuit diagram which implements the principles of the disclosure. Similarly, a flow chart, a program flow diagram, a state transition diagram, a pseudo-code and the like can represent different processes, operations or steps which are essentially represented, for example, in computer-readable medium and thus executed by a computer or processor, regardless of whether such a computer or processor is explicitly shown. Methods disclosed in the description or in the patent claims can be implemented by a component which has a means for executing each one of the respective steps of these methods.

It goes without saying that the disclosure of a plurality of steps, processes, operations or functions disclosed in the description or the claims should not be interpreted as being in the specified order, unless this is explicitly or implicitly stated otherwise, for example, for technical reasons. Therefore, these are not limited by the disclosure of a plurality of steps or functions to a specific sequence unless for technical reasons these steps or functions are not interchangeable. Also, in some examples a single step, function, process or operation can include a plurality of sub-steps, sub-functions, sub-processes or sub-operations and/or be broken down into the same. Such sub-steps can be included and form part of the disclosure of this single step, unless they are explicitly excluded.

In addition, the following claims are hereby incorporated into the detailed description, where each claim can stand for a separate example in itself. While each claim can stand as a separate example in itself, it is important to note that, although a dependent claim in the claims may relate to a specific combination with one or more other claims—other examples may also comprise a combination of the dependent claim with the subject matter of any other dependent or independent claim. Such combinations are explicitly proposed here, unless it is specified that a certain combination is not intended. In addition, features of a claim should also be included for any other independent claim, even if this claim is not directly made dependent on the independent claim.

What is claimed is:

1. A tomography apparatus, comprising:
 a first semiconductor device with a first radar transceiver integrated circuit (IC), a second semiconductor device with a second radar transceiver IC, and at least one third semiconductor device with a third radar transceiver IC, which are arranged at different positions around a tomographical measurement region;

a synchronization circuit configured to provide a synchronization signal in order to operate the first radar transceiver IC as a master, the second radar transceiver IC as a synchronized slave, and the third radar transceiver IC as another synchronized slave by using the synchronization signal; and an evaluation circuit configured to ascertain at least one characteristic of a medium located in the tomographical measurement region based on time-of-flight measurements of radar signals received from at least two receivers.

2. The tomography apparatus as claimed in claim 1, wherein the first radar transceiver IC is configured to generate a local oscillator signal and wherein the synchronization signal is based on the local oscillator signal of the first radar transceiver IC.

3. The tomography apparatus as claimed in claim 1, wherein the synchronization circuit is configured to divide down a frequency of a local oscillator signal, in order to obtain a divided-down local oscillator signal and distribute the divided-down local oscillator signal as the synchronization signal, and to transform a frequency of the synchronization signal back up again in the slaves.

4. The tomography apparatus as claimed in claim 2, wherein the first radar transceiver IC is configured to generate the local oscillator signal as an FMCW signal.

5. The tomography apparatus as claimed in claim 1, wherein the synchronization signal is based on a clock signal of the first radar transceiver IC and the synchronization circuit is configured to generate respective local oscillator signals in the first radar transceiver IC, the second radar transceiver IC, and the third radar transceiver IC based on the clock signal.

6. The tomography apparatus as claimed in claim 1, wherein the evaluation circuit is configured to ascertain the at least one characteristic of the medium based on a difference between a propagation-time measurement and a calibration propagation-time measurement.

7. The tomography apparatus as claimed in claim 1, wherein the evaluation circuit is configured to ascertain the at least one characteristic of the medium, based on at least one of a phase difference or a power difference between a transmission signal of the first radar transceiver IC and a received signal of at least one of the second radar transceiver IC or third radar transceiver IC.

8. The tomography apparatus as claimed in claim 1, further comprising a control circuit, which is configured to operate the first radar transceiver IC, the second radar transceiver IC, and the third radar transceiver IC as a transmitter and receiver according to a multiplexing method.

9. The tomography apparatus as claimed in claim 8, wherein the multiplexing method comprises a frequency-division multiplexing, time-division multiplexing, code-division multiplexing method, or a combination thereof.

10. The tomography apparatus as claimed in claim 1, wherein each of the first, the second, and the third radar transceiver ICs has an integrated fast fourier transform (FFT) circuit which is configured to subject a respective baseband reception signal to an FFT in order to obtain an FFT signal.

11. The tomography apparatus as claimed in claim 10, wherein each of the first, the second, and the third radar transceiver ICs is configured to forward a respective FFT signal to the evaluation circuit and wherein the evaluation circuit is configured to ascertain the medium from a combination of the respective FFT signals.

12. The tomography apparatus as claimed in claim 1, wherein the medium is located in a container which is non-transparent to the radar signals and has transmission regions for the radar signals at different positions of the first, the second, and the third radar transceiver ICs.

13. The tomography apparatus as claimed in claim 1, wherein the radar transceiver ICs are each coupled to antennas, which each have a directional characteristic that is matched to a distribution of the radar transceiver ICs around the medium.

14. The tomography apparatus of claim 1, wherein the first radar transceiver IC is configured to generate a local oscillator signal and distribute the local oscillator signal.

15. The tomography apparatus of claim 1, wherein the first radar transceiver IC is configured to generate a local oscillator signal and distribute the synchronization signal to the second radar transceiver IC and the third radar transceiver IC.

16. A tomography method comprising:

arranging a first semiconductor device with a first radar transceiver integrated circuit (IC), a second semiconductor device with a second radar transceiver IC and at least one third semiconductor device with a third radar transceiver IC at different positions around a tomographical measurement region;

distributing a synchronization signal in order to operate the first radar transceiver IC as a master, the second radar transceiver IC as a synchronized slave, and the third radar transceiver IC as another synchronized slave using the synchronization signal; and evaluating time-of-flight measurements of radar signals received from at least of two receivers, in order to ascertain a characteristic of a medium located in the tomographical measurement region.

17. The tomography method as claimed in claim 16, wherein in the first radar transceiver IC a local oscillator signal is generated, on which the synchronization signal is based.

18. The tomography method as claimed in claim 17, wherein the local oscillator signal is generated as an FMCW radar signal.

19. The tomography method as claimed in claim 16, wherein for a tomography of the medium the first, the second, and the third radar transceiver ICs are operated as transmitters and receivers in accordance with a multiplexing method.

20. The tomography method as claimed in claim 16, wherein the characteristic of the medium is ascertained based on a phase difference and/or a power difference between a transmission signal of the first radar transceiver IC and a received signal of at least one of the second transceiver IC or the third radar transceiver IC.

* * * * *